United States Patent [19]

Brake et al.

[11] Patent Number: 5,264,626
[45] Date of Patent: Nov. 23, 1993

[54] RAPID DEPOLYMERIZATION OF POLYHYDROXY ACIDS

[75] Inventors: Loren D. Brake, Wilmington; Narayanan S. Subramanian, Hockessin, both of Del.

[73] Assignee: E. I. Du Pont de Nemours and Company, Wilmington, Del.

[21] Appl. No.: 797,503

[22] Filed: Nov. 22, 1991

[51] Int. Cl.$^5$ .................... C07C 59/08; C07C 51/42
[52] U.S. Cl. .................... 562/589; 562/580; 549/274; 528/490; 528/487; 528/499; 525/450
[58] Field of Search ............... 562/589, 580; 549/274; 528/300

[56] References Cited

U.S. PATENT DOCUMENTS

| | | | |
|---|---|---|---|
| 2,231,953 | 2/1941 | Ruxicka | 92/17 |
| 3,284,417 | 11/1966 | Hostettler et al. | 260/78.3 |
| 3,578,700 | 5/1971 | Klootwijk et al. | 260/484 |
| 4,727,163 | 2/1988 | Bellis | 549/274 |
| 4,797,468 | 1/1989 | De Vries | 528/354 |
| 4,835,293 | 5/1989 | Bhatia | 549/274 |

FOREIGN PATENT DOCUMENTS

90/01521  2/1990  PCT Int'l Appl. .

Primary Examiner—José G. Dees
Assistant Examiner—Porfirio Nazario

[57] ABSTRACT

Rapid recovery from waste of high molecular weight polyhydroxyacid content by depolymerizing the PHA in acidic water.

12 Claims, No Drawings

RAPID DEPOLYMERIZATION OF POLYHYDROXY ACIDS

BACKGROUND OF THE INVENTION

1. Field of the Invention

The present invention relates to the depolymerization of a high molecular weight polyhydroxy acid (PHA) by heating under pressure in water and acid and the subsequent recovery of a liquid phase having monomer/oligomer polyhydroxy/hydroxy acid value. More specifically, the invention relates to the recovery of monomer-/oligomer polyhydroxy acid value from a polyhydroxy acid polymer-containing source such as food container trash.

2. Description of the Related Art

Shaped articles of high molecular weight (at least 10,000, and normally 15,000 to 500,000 MW) polyhydroxy acids (PHA), particularly as polylactic acid (PLA, polylactide), and polyglycolic acid (PGA, polyglycolide), and copolymers thereof, have been known for years. An important property of these polymers is that they are slowly hydrolyzable and thereafter biodegradable to environmentally benign by-products. Consequently high molecular weight PHA polymer shaped articles are finding increasing application as replacements for polystyrene and other non-degradable polymers in products that will degrade in a landfill, such as fast food containers (Sinclair et al., WO90/01521, Feb. 22, 1990).

While this is a significant step in minimizing litter and long-term landfill disposal, discarding high molecular weight polyhydroxy acid articles for natural destruction by hydrolysis has the cost penalty of discarding the valuable polyhydroxy acid.

Although the hydrolysis of PHAs is well known, heretofore it has not been achievable in a time frame to permit recovery from other insoluble waste and reuse of the valuable hydroxy acid (HA) moities. In fact, although degradable, the time for degradation of high molecular weight PHAs is so long as not to offer a significant lessening burden on landfills.

Thus, there is a need for an economical method to recover and recycle the polyhydroxy acid content of this source of insoluble waste material and avoid burdening landfills with this waste.

The most economical routes for PHA production start with the acid such as lactic acid. The acid is converted to an ester, dimerized to a cyclic ring such as lactide, which is then polymerized to PHA. This is a complicated and costly process. See U.S. Pat. Nos. 4,835,293 Bhatia (May 30, 1989); Bellis 4,727,163 (Feb. 23, 1988); Klootwijk 3,578,700 Hostettler et al. 3,284,417; and De Vries 4,797,468 (Jan. 10, 1989).

Bhatia, U.S. Pat. No. 5,136,057, discloses the depolymerization of low molecular weight oligomers remaining after PHA polymerization. This patent application does not address the problem of recovery of the monomeric values from used high molecular weight PHA articles.

Copending and commonly assigned U.S. patent applications Ser. Nos. 07/797,502, 07/796,273, 07/796,272 and 07/796,274 disclose the recovery of PHAs, respectively, in the presence of an alcohol and an acid catalyst; in water under heat and pressure; in the presence of specific amines; and in the presence of water and lower alkyl alcohol.

The aforementioned patents and patent applications are incorporated herein by reference.

SUMMARY OF THE INVENTION

The present invention provides a method of recovering high molecular weight polyhydroxy acid polymer comprising the step of:
(a) mixing the polymer with water containing a small amount of a strong acid present in an amount of at least 1 mole of water per mole hydroxy acid equivalent of the polyhydroxy acid; and
(b) heating the mixture to at least partially depolymerize and liquidify the PHA.

In one embodiment of the invention the polymer is selected from group consisting of polylactide, polyglycolide, and polymers containing a major proportion of polylactide and polyglycolide polymerized with up to 30% of another monomer selected from the group consisting of epsilon-caprolactone, delta-valerolactone, 1,5-dioxepen-2-one, 1,4-dioxan-2-one, beta-butyrolactone and mixtures thereof. Typically the temperature of the process is in the range of 100° to 200° C. and the time for conversion is in the range of $\frac{1}{4}$ to 16 hours.

The present invention further provides a process for recovering polyhydroxy acid and hydroxy acid value from a polyhydroxy acid polymer-containing source comprising the steps of:
(a) contacting a polyhydroxy acid polymer-containing material, wherein said polyhydroxy acid polymer-containing material is contaminated with or constitutes trash, with at least one mole of water per mole of hydroxy acid equivalent of said polyhydroxy acid polymer, wherein the water contains an effective amount of a strong acid, and while maintaining the resulting mixture at sufficient temperature and pressure for a sufficient time to depolymerize said polymer and form a liquid phase of enhanced monomer and oligomer hydroxy acid value; and
(b) thereafter isolating and recovering said liquid phase.

DESCRIPTION OF THE PREFERRED EMBODIMENTS

The present invention is a process for economically rapid recovery of the valuable PHA content of high molecular weight PHAs, thereby recycling instead of landfilling the PHA products, particularly fast food containers such as plates, cups, and solid food containers.

Specifically, the present invention relates to the recovery of high molecular weight PHAs of at least 10,000 and normally 15,000 to 500,000 MW by at least partially depolymerizing the PHA content in acidified water at elevated temperature to yield the depolymerization product as an aqueous fluid. The depolymerization aqueous fluid can be used directly, or with some water removal concentration, in the preparation of high molecular weight PHA.

The depolymerization product is a low molecular weight oligomer, the average molecular weight depending on the depolymerization conditions of time, temperature and pressure of heating and the water/acid content of the dissolving liquid. Preferably, depolymerization is continued long enough to yield a PHA depolymerization product at a concentration of at least 10%, preferably greater than 70%, in the acidic water that can be handled as a liquid.

This process is used for the depolymerization of high molecular weight PHAs, and co- and ter-polymers therewith. It is most useful in the depolymerization of polylactide, polyglycolide and copolymers thereof; also it is useful for PHAs containing these polymer moities polymerized with other monomers. These co- and ter-polymers preferably contain at least 70% of PLA and PGA moities, and not more than 30% of the other monomer. Examples of other suitable monomer units are:

epsilon-caprolactone,
delta-valerolactone,
1,5-dioxepan-2-one,
1,4-dioxan-2-one,
beta-butyrolactone,
beta-propiolactone, and
6-methyl-2,5-morpholinedione.

Other monomer units present in minor percents in the PHA to be depolymerized are not critical, the present process having wide applicability in depolymerizing, fluidizing, and recovering the monomer/oligomer value of PHAs.

The amount of water and the acid content used affects the time required to carry out the necessary depolymerization. Normally a molar ratio of water to PHA (on a PHA acid unit basis) in the range of 1:1 to 5:1, preferably 1.5:1 to 2:1, is used. Since an excess of water favors depolymerization, preferably a substantial excess is used, but not so much as to make product concentration an excessive expense.

Various acids are effective in the present process. In general strong organic or inorganic acids that do not react with the PHA to form depolymerization products or form undesirable by-products can be used. Liquid or water soluble solid catalysts are preferred for ease of use and concentration. Sulfuric acid (6-36N) and p-toluene sulfonic acid (solid) are excellent inexpensive acid catalysts. Methane sulfonic acid is also acceptable. Hydrochloric acid, although effective, is generally undesirable because of its excessive corrosiveness to equipment. Very small quantities of acid are required, normally in the weight range of 0.01 to 4% by weight of acid molecule or more, preferably 0.1% to 1.0% of the PHA to be catalytically effective. The depolymerization proceeds even if large quantities of water are introduced with the acid (dilute acid).

An important aspect of the present invention is to use temperatures, and so pressures, adequate to cause the rapid depolymerization and dissolving of the PHAs, but not severe enough to form undesirable degradation products. Temperatures normally in the range of 75° to 250° C. or higher, preferably 100° to 200° C. are employed. In many cases overall economics and reaction kinetics dictate running the process at atmospheric pressure although elevated pressure sometimes is needed to reach the necessary temperatures for depolymerization. However, it may be desirable to use elevated pressures up to about 500 psi or higher, preferably 50 to 150 psi, when high rates are desired. Normally autogenous pressure is adequate.

By selecting optimal reaction conditions, particularly pressure and temperature, significant quantities of PHA can be adequately depolymerized and solubilized by a batch process often in 1 hour and even in as little as 15 minutes. Reactor design, i.e., agitation, etc., also plays an important role in reaction rate. Where speed is less a factor than other economies, batch times as long as 16 hours may be appropriate.

Continuous process depolymerization and liquifaction is also possible, such as with the feed materials being continuously introduced into the first depolymerization stage of a multistage system, and the low molecular weight liquid product being recovered from the last stage.

The following examples illustrate the preferred practice of the present invention.

EXAMPLE 1

A mixture of 75 grams polylactide (300,000 M.W.), 38 grams water and 0.5 gram concentrated sulfuric acid is heated at 150° C. for one hour in a pressure vessel under autogenous pressure of 75 psig. The product is fluid than can be easily pumped and transported for conversion to polymer for reuse.

EXAMPLE 2

A mixture of 75 grams polylactide, 38 grams water and 0.3 grams p-toluenesulfonic acid is heated at 170° C. for 30 minutes in a pressure vessel under autogenous pressure. The polylactide depolymerizes to lactic acid and low molecular weight oligomers as a liquid that can be pumped and transported for conversion to polymer for reuse.

EXAMPLE 3

A mixture of 100 grams polylactide, 50 grams water and 0.2 grams methanesulfonic acid is heated at 180° C. for one hour in a pressure vessel under autogenous pressure. The polylactide depolymerizes to lactic acid and low molecular weight oligomers aqueous liquid that can be pumped and transported for conversion to oligomer for reuse.

EXAMPLE 4-8

The following series of Examples compare the time needed to depolymerize 75 grams polylactide, 38 grams water and 0.5 grams concentrated sulfuric acid in a pressure vessel under autogenous pressure.

| Example | Temperature/Time | Results |
|---------|------------------|---------|
| 4 | 100° C./5 days | Trace depolymerization |
| 5 | 130° C./2 hours | Incomplete liquidifaction |
| 6 | 150° C./2 hours | Fluid |
| 7 | 150° C./1 hour | Fluid |
| 8 | 170° C./30 minute | Fluid |

EXAMPLE 9-12

The process of Example 2 is repeated using the following polymer ingredient with similar results.

| Example | Polymer |
|---------|---------|
| 9 | Copolymer of 80% lactic acid and 20% glycolic acid |
| 10 | Copolymer of 90% lactic acid and 10% glycolic acid |
| 11 | Copolymer of 80% lactic acid and 20% epsilon-caprolactone |
| 12 | Copolymer of 90% lactic acid and 10% beta-propiolactone |

What is claimed is:

1. The process of recovering the hydroxy acid content from a high molecular weight polyhydroxy acid polymer comprising:
   (a) mixing the polyhydroxy acid polymer with water containing a small amount of a strong acid, said water being present in an amount of at least 1 mole of water per mole of hydroxy acid equivalent present in said polyhydroxy acid polymer; and (b) subjecting the resulting mixture to a temperature and pressure sufficient to at least partially depolymerize the polyhydroxy acid polymer, said temperature and pressure being insufficient to form undesirable degradation products.

2. The process of claim 1 wherein the mixture is heated to 100° to 200° C.

3. The process of claim 1 wherein the mixture is heated under autogenous pressure.

4. The process of claim 1 wherein the acid catalyst concentration is 0.1% to 4.0% by weight of the water.

5. The process of claim 1 wherein the polymer contains at least a major proportion of polylactide.

6. The process of claim 1 wherein the polymer is polylactide.

7. The process of claim 1 wherein said polymer is selected from the group consisting of polylactide, polyglycolide, and polymers containing a major proportion of polylactide and polyglycolide polymerized with up to 30% of another monomer selected from the group consisting of epsilon-caprolactone, delta-valerolactone, 1,5-dioxepen-2-one, 1,4-dioxan-2-one, beta-butyrolactone.

8. The process of claim 2 wherein the time of heating is in the range of ¼–16 hours.

9. The process of claim 1 wherein the acid is selected from the group consisting of sulfuric, p-toluene sulfonic and methane sulfonic acids.

10. The process of claim 1 wherein depolymerization is continued long enough to yield a depolymerization product at a concentration of at least 10% in the acidic water.

11. The process of claim 1 additionally comprising:
(c) concentrating the product of step (b) by removal of water.

12. A process for recovering polyhydroxy acid and hydroxy acid value from a polyhydroxy acid polymer-containing source comprising the steps of:

(a) contacting a polyhydroxy acid polymer-containing material, wherein said polyhydroxy acid polymer-containing material is contaminated with or constitutes trash, with at least one mole of water per mole of hydroxy acid equivalent of said polyhydroxy acid polymer, wherein said water contains an effective amount of a strong acid, and while maintaining the resulting mixture at sufficient temperature and pressure for a sufficient time to depolymerize said polymer and form a liquid phase of enhanced monomer and oligomer hydroxy acid value, said temperature and pressure being insufficient to form undesirable degradation products; and (b) thereafter isolating and recovering said liquid phase.

* * * * *